United States Patent
Asina et al.

(10) Patent No.: US 7,297,331 B2
(45) Date of Patent: Nov. 20, 2007

(54) BEADS CONTAINING RESTRICTED CANCER CELLS PRODUCING MATERIAL SUPPRESSING CANCER CELL PROLIFERATION

(75) Inventors: Shirin Asina, New York, NY (US); Kanti Jain, New York, NY (US); Albert L. Rubin, Englewood, NJ (US); Barry Smith, New York, NY (US); Kurt Stenzel, New York, NY (US)

(73) Assignee: The Rogosin Institute, New York, NY (US)

( * ) Notice: Subject to any disclaimer, the term of this patent is extended or adjusted under 35 U.S.C. 154(b) by 402 days.

(21) Appl. No.: 10/919,767

(22) Filed: Aug. 16, 2004

(65) Prior Publication Data

US 2005/0037029 A1    Feb. 17, 2005

Related U.S. Application Data

(60) Division of application No. 10/336,313, filed on Jan. 3, 2003, now Pat. No. 6,818,230, which is a continuation-in-part of application No. 08/745,063, filed on Nov. 7, 1996, now Pat. No. 5,888,497, which is a continuation-in-part of application No. 08/625,595, filed on Apr. 3, 1996, now abandoned.

(51) Int. Cl.
*A61K 35/12* (2006.01)
*C12N 11/02* (2006.01)
*C12N 11/10* (2006.01)
*C12N 5/00* (2006.01)
*C12N 5/08* (2006.01)

(52) U.S. Cl. ............ 424/93.7; 435/177; 435/178; 435/182; 435/366; 435/382; 435/395; 435/397

(58) Field of Classification Search .............. None
See application file for complete search history.

(56) References Cited

U.S. PATENT DOCUMENTS

| | | | |
|---|---|---|---|
| 3,865,689 A | 2/1975 | Goldenberg | 195/1.7 |
| 4,285,930 A | 8/1981 | Likhite et al. | 424/92 |
| 4,352,883 A | 10/1982 | Lim | 435/178 |
| 4,391,909 A | 7/1983 | Lim | 435/178 |
| 4,409,331 A | 10/1983 | Lim | 435/178 |
| 4,647,536 A | 3/1987 | Mosbach et al. | 435/177 |
| 4,663,286 A | 5/1987 | Tsang et al. | 435/178 |
| 4,673,566 A | 6/1987 | Goosen et al. | 424/19 |
| 4,680,174 A | 7/1987 | Jarvis, Jr. et al. | 424/85 |
| 4,798,786 A | 1/1989 | Tice et al. | 435/177 |
| 4,902,295 A | 2/1990 | Walthall et al. | 623/11 |
| 4,971,833 A | 11/1990 | Larsson et al. | 427/213.33 |
| 4,997,443 A | 3/1991 | Walthall et al. | 623/11 |
| 5,053,332 A | 10/1991 | Cook et al. | 435/178 |
| 5,227,298 A | 7/1993 | Weber et al. | 435/178 |
| 5,428,012 A | 6/1995 | Shoyab et al. | |
| 5,639,275 A | 6/1997 | Baetge et al. | 604/891.1 |
| 5,800,828 A | 9/1998 | Dionne et al. | |
| 5,800,829 A | 9/1998 | Dionne et al. | |
| 5,834,001 A | 11/1998 | Dionne et al. | |
| 5,869,077 A | 2/1999 | Dionne et al. | |
| 5,871,767 A | 2/1999 | Dionne et al. | |
| 5,874,099 A | 2/1999 | Dionne et al. | |
| 5,888,497 A * | 3/1999 | Jain et al. | 424/93.7 |
| 6,224,912 B1 * | 5/2001 | Asina et al. | 424/520 |
| RE38,027 E * | 3/2003 | Jain et al. | 424/93.7 |
| 6,818,230 B2 * | 11/2004 | Asina et al. | 424/520 |

FOREIGN PATENT DOCUMENTS

| | | |
|---|---|---|
| JP | 59-33223 | 2/1984 |
| JP | 61-18721 | 1/1986 |
| JP | X-002256191 | 4/1988 |
| JP | 64-63395 | 3/1989 |
| JP | 2-16994 | 1/1990 |
| WO | WO 95/19430 | 7/1995 |
| WO | WO 95/28480 | 10/1995 |
| WO | 9601611 | 1/1996 |
| WO | 9736495 | 9/1997 |

OTHER PUBLICATIONS

Brodelius et al., "Entrapment of Plant Cells in Different Matrices", FEBS Letters: 122(2) : 312-316 (1980).

Disalvo, et al., "Purification and characterization of a naturally occurring vascular endothelial growth factor—placenta growth factor heterodimer", J. Biol. Chem., vol. 270, No. 13, pp. 7717-7723, Mar. 31, 1995.

O'Connell, et al., "Cellular proliferation and activation of NFkB are induced by autocrine production of tumor necrosis factor α in the human T lymphoma line HuT 78", J. Biol. Chem., vol. 270, No. 13, pp. 7399-7404, Mar. 31, 1995.

Visser, et al.: "Proliferation of gubemaculum cells induced by a substance of low molecular mass obtained from fetal pig testes", *The Journal of Urology*, vol. 153, 516-520, Feb. 1995.

Angiostatin: A Novel Angiogenesis Inhibitor That Mediates the Suppression . . . Carcinoma, Cell, Michael S. O'Reilly, et al., vol. 79, 315-328, Oct. 1994.

Journal of Biomedical Materials Research, Iwata, et al. vol. 26 (1992).

* cited by examiner

*Primary Examiner*—David M. Naff
(74) *Attorney, Agent, or Firm*—Fulbright & Jaworski L.L.P.

(57) ABSTRACT

Compositions of matter are described which contain restricted cancer cells. When so restricted, the cells produce an unexpectedly high amount of material which suppresses cancer cell proliferation. The phenomenon crosses cancer type and species lines. Processes for making these compositions, and their use, are also described.

8 Claims, No Drawings

BEADS CONTAINING RESTRICTED CANCER CELLS PRODUCING MATERIAL SUPPRESSING CANCER CELL PROLIFERATION

RELATED APPLICATION

This application is a divisional of U.S. Ser. No. 10/336,313 filed Jan. 3, 2003, now U.S. Pat. No. 6,818,230, which is continuation-in-part of allowed patent application Ser. No. 08/745,063, filed on Nov. 7, 1996, now U.S. Pat. No. 5,888,497 which is a continuation-in-part of patent application Ser. No. 08/625,595, filed Apr. 3, 1996, abandoned, each of which are incorporated hereby by reference in their entireties.

FIELD OF THE INVENTION

The present invention relates to the restriction of the proliferation of cancer cells to produce material which suppresses proliferation of unrestricted cancer cells. The structures which are one feature of the invention can be used "as is," or to produce material such as concentrates with a minimum approximate molecular weight, which also have an anti-proliferative effect on cancer.

BACKGROUND AND PRIOR ART

The encapsulation of various biological materials in biologically compatible materials, which is well documented in the literature, is a technique that has been used for some time, albeit with limited success. Exemplary of the art are U.S. Pat. No. 5,227,298 (Weber, et al.); U.S. Pat. No. 5,053,332 (Cook, et al.); U.S. Pat. No. 4,997,443 (Walthall, et al.); U.S. Pat. No. 4,971,833 (Larsson, et al.); U.S. Pat. No. 4,902,295 (Walthall, et al.); U.S. Pat. No. 4,798,786 (Tice, et al.); U.S. Pat. No. 4,673,566 (Goosen, et al.); U.S. Pat. No. 4,647,536 (Mosbach, et al.); U.S. Pat. No. 4,409,331 (Lim); U.S. Pat. No. 4,392,909 (Lim); U.S. Pat. No. 4,352,883 (Lim); and U.S. Pat. No. 4,663,286 (Tsang, et al.). Also of note is U.S. Pat. No. 5,643,569 to Jain, et al., incorporated by reference herein. Jain, et al. discuss, in some detail, the encapsulation of islets in various biocompatible materials. Islets produce insulin, and the use of the materials disclosed by Jain, et al. in the treatment of diabetes is taught therein.

The Jain, et al. patent discusses, in some detail, the prior approaches taken by the art in transplantation therapy. These are summarized herein as well.

Five major approaches to protecting the transplanted tissue from the host's immune response are known. All involve attempts to isolate the transplanted tissue from the host's immune system. The immunoisolation techniques used to date include: extravascular diffusion chambers, intravascular diffusion chambers, intravascular ultrafiltration chambers, microencapsulation, and macroencapsulation. There are many problems associated with methods of the prior art, including a host fibrotic response to the implant material, instability of the implant material, limited nutrient diffusion across semi-permeable membranes, secretagogue and product permeability, and diffusion lag-time across semi-permeable membrane barriers.

For example, a microencapsulation procedure for enclosing viable cells, tissues, and other labile membranes within a semipermeable membrane was developed by Lim in 1978. (Lim, Research report to Damon Corporation (1978)). Lim used microcapsules of alginate and poly L-lysine to encapsulate the islets of Langerhans. In 1980, the first successful in vivo application of this novel technique in diabetes research was reported (Lim, et al., *Science* 210: 908 (1980)). The implantation of these microencapsulated islets of Langerhans resulted in sustaining a euglycemic state in diabetic animals. Other investigators, however, repeating these experiments, found the alginate to cause a tissue reaction and were unable to reproduce Lim, et al.'s results (Lamberti, et al. *Applied Biochemistry and Biotechnology* 10: 101 (1984); Dupuy, et al., *J. Biomed. Material and Res.* 22: 1061 (1988); Weber, et al., *Transplantation* 49: 396 (1990); and Doon-shiong, et al., *Transplantation Proceedings* 22: 754 (1990)). The water solubility of these polymers is now considered to be responsible for the limited stability and biocompatibility of these microcapsules in vivo (Dupuy, et al., supra, Weber et al., supra, Doon-shiong, et al., supra, and Smidsrod, *Faraday Discussion of Chemical Society* 57: 263 (1974)).

Iwata et al., (Iwata, et al. *Jour. Biomedical Material and Res.* 26: 967 (1992)) utilized agarose for microencapsulation of allogeneic pancreatic islets and discovered that it could be used as a medium for the preparation of microbeads. In their study, 1500-2000 islets were microencapsulated individually in 5% agarose and implanted into streptozotocin-induced diabetic mice. The graft survived for a long period of time, and the recipients maintained normoglycemia indefinitely.

Their method, however, suffers from a number of drawbacks. It is cumbersome and inaccurate. For example, many beads remain partially coated and several hundred beads of empty agarose form. Additional time is thus required to separate encapsulated islets from empty beads. Moreover, most of the implanted microbeads gather in the pelvic cavity, and a large number of islets in completely coated individual beads are required to achieve normoglycemia. Furthermore, the transplanted beads are difficult to retrieve, tend to be fragile, and will easily release islets upon slight damage.

A macroencapsulation procedure has also been tested. Macrocapsules of various different materials, such as poly-2-hydroxyethyl-methacrylate, polyvinylchloride-c-acrylic acid, and cellulose acetate were made for the immunoisolation of islets of Langerhans. (See Altman, et al., *Diabetes* 35: 625 (1986); Altman, et al., *Transplantation: American Society of Artificial Internal Organs* 30: 382 (1984); Ronel, et al., *Jour. Biomedical Material Research* 17: 855 (1983); Klomp, et al., *Jour. Biomedical Material Research* 17: 865-871 (1983)). In all these studies, only a transitory normalization of glycemia was achieved.

Archer, et al., *Journal of Surgical Research* 28: 77 (1980), used acrylic copolymer hollow fibers to temporarily prevent rejection of islet xenografts. They reported long-term survival of dispersed neonatal murine pancreatic grafts in hollow fibers which were transplanted into diabetic hamsters. Recently Lacy, et al., *Science* 254: 1782-1784 (1991) confirmed their results, but found the euglycemic state to be a transient phase. They found that when the islets are injected into the fiber, they aggregate within the hollow tube with resultant necrosis in the central portion of the islet masses. The central necrosis precluded prolongation of the graft. To solve this problem, they used alginate to disperse the islets in the fiber. However, this experiment has not been repeated extensively. Therefore, the membrane's function as an islet transplantation medium in humans is questionable.

The Jain, et al. patent discussed reports that encapsulating secretory cells in a permeable, hydrophilic gel material results in a functional, non-immunogenic material, that can be transplanted into animals, can be stored for long lengths of time, and is therapeutically useful in vivo. The macroencapsulation of the secretory cells provided a more effective and manageable technique for secretory cell transplantation.

The patent does not discuss at any length the incorporation of cancer cells. A survey of the literature on encapsulation of cells reveals that, following encapsulation, cells almost always produce less of materials than they produce when not encapsulated. See Lloyd-George, et al., *Biomat. Art. Cells & Immob. Biotech*. 21(3): 323-333 (1993); Schinstine, et al., *Cell Transplant* 4(1): 93-102 (1995); Chicheportiche, et al., *Diabetologica* 31:54-57 (1988); Jaeger, et al., *Progress In Brain Research* 82:41-46 (1990); Zekorn, et al., *Diabetologica* 29:99-106 (1992); Zhou, et al., *Am. J. Physiol*. 274: C1356-1362 (1998); Darquy, et al., *Diabetologica* 28:776-780 (1985); Tse, et al., *Biotech. & Bioeng*. 51:271-280 (1996); Jaeger, et al., *J. Neurol*. 21:469-480 (1992); Hortelano, et al., *Blood* 87(12): 5095-5103 (1996); Gardiner, et al., *Transp. Proc*. 29:2019-2020 (1997). None of these references deal with the incorporation of cancer cells into a structure which entraps them and restricts their growth, but nonetheless permit diffusion of materials into and out of the structure.

One theory relating to the growth of cancerous masses likens such masses, e.g., tumors, to normal organs. Healthy organs, e.g. the liver, grow to a particular size, and then grow no larger; however, if a portion of the liver is removed, it will regenerate to a certain extent. This phenomenon is also observed with tumors. To summarize, it has been noted that, if a portion of a tumor is removed, the cells in the remaining portion of the tumor will begin to proliferate very rapidly until the resulting tumor reaches a particular size, after which proliferation slows down, or ceases. This suggests that there is some internal regulation of cancer cells.

SUMMARY OF THE INVENTION

The invention, which will be seen in the following disclosure, shows that when cancer cells are restricted by being entrapped, their proliferation is halted, and they produce unexpectedly high amounts of material which, when applied to non-restricted cancer cells, inhibits the proliferation of these non-restricted cancer cells. The ability to retard proliferation of cancer cells has been a goal of oncology since its inception. Hence, the therapeutic usefulness of this invention will be clear and will be elaborated upon herein. The material produced does not appear to be limited by the type of cancer cell used, nor by the animal species from which the cancer cells originate. Further, the effect does not appear to be species specific, as restricted cells from a first species produce material which inhibits proliferation of unrestricted cells from a second species. Also, the effect does not appear to be specific to the type of cancer, as restricted cells from a first cancer type produce material which inhibits proliferation of unrestricted cells from another cancer type.

Nor does the effect appear to require an immune response. The antiproliferative effect is seen in in vitro systems, where no immune cells are used. Hence the antiproliferative effect cannot be attributed to classical immunological responses.

Thus, a preferred embodiment of the invention relates to a composition of matter having a biocompatible, proliferation-restrictive, selectively-permeable structure. The structure restricts cancer cells which then produce more of a material which suppresses cancer cell proliferation compared to an equal number of the same cancer cells when unrestricted.

Another preferred embodiment of the present invention relates to a process for preparing a biocompatible, proliferation-restrictive, selectively-permeable structure, by forming a structure by contacting cancer cells with biocompatable, proliferation-restrictive matter to form the structure, and culturing the structures for a sufficient period of time to restrict the cancer cells such that they produce a material which suppresses cancer cell proliferation compared to an equal number of unrestricted cancer cells of the same cancer type.

Yet another preferred embodiment relates to a method of increasing the production of material that suppresses cancer cell growth by a cancer cell, comprising restricting cancer cells in a structure-forming material to form a biocompatable, selectively-permeable, proliferation-restrictive structure and culturing the cancer cells until they are restricted and produce the material.

It has also been found that a powerful antiproliferative effect can be achieved by subjecting conditioned medium obtained by culturing the structures of the invention in culture medium to filtration. The resulting concentrates have extremely strong anti-proliferative effects.

The material, the conditioned medium, and/or the concentrates derived therefrom may also be useful for inducing the production of the anti-proliferative material by other non-restricted cancer cells.

These, and other features of the invention, will be seen from the disclosure which follows.

DETAILED DESCRIPTION OF PREFERRED EMBODIMENTS

EXAMPLE 1

This example, and those which follow, employ RENCA cells. These are spontaneous renal adenocarcinoma cells of BALB/C mice, which are widely available, having been maintained in both in vitro cultures and in vivo. See Franco, et al., *Cytokine Induced Tumor Immunogenecity*, 181-193 (1994).

Samples of frozen RENCA cells were thawed at 37° C., and then placed in tissue culture flasks containing Dulbecco's Modified Medium (D-MEM), which had been supplemented with 10% bovine serum, penicillin (100 u/ml) and streptomycin (50 ug/ml), to give what will be referred to as "complete medium" hereafter.

Cells were grown to confluence, and then trypsinized, followed by washing with Hank's Balanced Salt Solution, and then with the complete medium referred to supra.

In order to determine if the RENCA cells produced tumors efficiently, two BALB/C mice were injected, intraperitoneally, with $10^6$ of these cells. The mice were observed, over a 3-4 week period. Clinically, they appeared healthy for the first two weeks, and exhibited normal activity. Thereafter, the clinical manifestations of cancer became evident. One mouse died after 23 days, and the second, after 25 days. Following death, the mice were examined, and numerous tumors of various size were observed. Some of the tumors exhibited hemorrhaging as well.

A sample of one tumor, taken from one of the mice, was fixed in 10% formalin for later histological examination.

EXAMPLE 2

Following the showing that the RENCA cells did grow in vivo, studies were carried out to determine if these cells grew when restricted in the structure of the invention.

RENCA cells were grown to confluency, as described supra, trypsinized, and washed, also as described above. Samples of between 60,000 and 90,000 cells were then prepared. The cells were then centrifuged, at 750 RPMs, and fluid was removed. The cells were then suspended in solutions of 1% atelocollagen, in phosphate buffered saline solution, at a pH of 6.5.

A 1% solution of low viscosity agarose was prepared in minimal essential medium (MEM), maintained at 60° C., and then 100 ul of this was added to the suspension of RENCA cells and atelocollagen, described supra. The materials were then transferred, immediately, as a single large droplet, into sterile, room-temperature mineral oil. The mixture formed a single, smooth, semi-solid bead. This procedure was repeated to produce a number of beads.

After one minute, the beads were transferred to complete medium, as described supra, at 37° C. The beads were then washed three times in Minimal Essential Medium (MEM) containing the antibiotics listed supra. The beads were then incubated overnight at 37° C., in a humidified atmosphere of air and 5% $CO_2$. Following the incubation the beads, now solid, were transferred to a sterile spoon which contained 1 ml of 5% agarose in MEM. Beads were rolled in the solution 2-3 times to uniformly coat them with agarose. The beads were transferred to mineral oil before the agarose solidified, to yield a smooth outer surface. After 60 seconds, the beads were washed, five times, with complete medium at 37° C. to remove the oil. Overnight incubation (37° C., humidified atmosphere of air, 5% $CO_2$) followed.

These RENCA containing beads were used in the experiments which follow.

EXAMPLE 3

Prior to carrying out in vivo investigations, it was necessary to determine if the RENCA cells would grow in beads prepared in the manner described supra.

To do this, beads prepared as discussed in example 2 were incubated in the medium described in example 2, for a period of three weeks, under the described conditions. Three of the beads were then cut into small pieces, and cultured in standard culture flasks, affording direct contact with both the flask and culture medium.

Observation of these cultures indicated that the cells grew and formed standard RENCA colonies. This indicated that the cells had remained viable in the beads.

EXAMPLE 4

In vivo experiments were then carried out. In these experiments, the beads were incubated for seven days, at 37° C. Subject mice then received bead transplants. To do this, each of four mice received a midline incision, carried through intraperitoneally. Three beads, each of which contained 60,000 RENCA cells were transplanted. Incisions were then closed (two-layer closure), using an absorbable suture. The four mice (BALB/C) were normal, male mice, weighing between 24-26 grams, and appeared to be healthy. Two sets of controls were set up. In the first set, two mice received three beads containing no RENCA cells, and in the second, two mice were not treated with anything.

Three weeks after the implantation, all of the mice received intraperitoneal injections of $10^6$ RENCA cells. Eighteen days later, one control mouse died. All remaining mice were then sacrificed, and evaluated for the presence or absence of tumor.

Control mice showed numerous tumors, while the mice which received the implants of bead-encapsulated cells showed only isolated small nodules throughout the cavity.

These encouraging results suggested the design of the experiments set forth in the following example.

EXAMPLE 5

In these experiments, established cancers were simulated by injecting RENCA cells under one kidney capsule of each of six BALB/C mice. Fifteen days later, mice were divided into two groups. The three mice in the first group each received three beads, as described in example 4, supra. The second group (the control group) received beads which did not contain RENCA cells.

For the initial 4-5 days, mice which had received RENCA cell containing implants looked lethargic, and their fur had become spiky. Thereafter, they returned to normal. The control group remained energetic, with no change in condition of fur.

Ten days after implantation (25 days after injection of RENCA cells), however, the control mice became sluggish and exhibited distended abdomens. One of the three control mice died at fourteen days following bead transplantation. Sacrifice of the mice followed.

The body cavities of the control mice showed profuse hemorrhaging, with numerous tumors all over the alimentary canal, liver, stomach and lungs. All organs of the abdominal cavity had become indistinguishable due to rampant tumor growth. The mice which had received beads with encapsulated RENCA cells, however showed no hemorrhaging, and only a few nodules on the alimentary canal. In addition, comparison of test and control groups showed that in the test group, nodules had not progressed beyond their initial growth under the kidney capsule and before macrobead implantation.

EXAMPLE 6

In vitro, freely inoculated RENCA cell growth is inhibited when such cells are incubated along with macrobead encapsulated RENCA cells. A further set of experiments was carried out to determine if this effect was observable with other cells.

An adenocarcinoma cell line, i.e., MMT (mouse mammary tumor), was obtained from the American Type Culture Collection. Encapsulated MMT cells were prepared, as described, supra with MMT cells, to produce beads containing 120,000 or 240,000 cells per bead. Following preparation of the beads, they were used to determine if they would inhibit proliferation of RENCA cells in vitro. Specifically, two six-well petri plates were prepared, via inoculation with $1 \times 10^4$ RENCA cells per well, in 4 ml of medium. In each plate, three wells served as control, and three as test. One of the three control wells in each plate received one empty bead. Each of the other wells received either two or three empty beads. The second set of wells was treated similarly, with wells receiving one, two or three beads containing 120,000 or 240,000 MMT cells. Wells were incubated at 37° C. for one week, after which RENCA cells were trypsinized, washed, and counted, using a hemocytometer. Results are shown in Table 1:

TABLE 1

|  | DISH #1 # of cells retrieved after one week | | DISH #2 # of cells retrieved after one week | |
| --- | --- | --- | --- | --- |
| Well # | Control (Empty macrobead) | 120,000 MMT cells | Control (Empty Macrobead) | 240,000 MMT cells |
| 1 | $2.4 \times 10^5$ | $1.4 \times 10^5$ | $2.8 \times 10^5$ | $1 \times 10^5$ |
| 2 | $2.0 \times 10^5$ | $1.2 \times 10^5$ | $3.6 \times 10^5$ | $7 \times 10^4$ |
| 3 | $4.4 \times 10^5$ | $1.25 \times 10^5$ | $2.5 \times 10^5$ | $9 \times 10^4$ |

EXAMPLE 7

Following the results in example 6, the same experiments was carried out using $1 \times 10^4$ MMT cells as the inoculant (i.e., the free cells) rather than RENCA cells. The experiment was carried out precisely as example 6. Results are set forth in Table 2 below.

TABLE 2

|  | DISH #1 | | DISH #2 | |
| --- | --- | --- | --- | --- |
| Well # | Control (Empty macrobead) | 120,000 MMT cells in macrobeads | Control (Empty Macrobead) | 240,000 MMT cells in macrobeads |
| 1 | $3.1 \times 10^6$ | $1.6 \times 10^6$ | $2.8 \times 10^6$ | $1.3 \times 10^6$ |
| 2 | $3.3 \times 10^6$ | $1.0 \times 10^6$ | $2.6 \times 10^6$ | $1.1 \times 10^6$ |
| 3 | $3.0 \times 10^6$ | $6.0 \times 10^5$ | $2.8 \times 10^6$ | $5.0 \times 10^5$ |

These results encouraged an in vivo experiment. This is presented in example 8.

EXAMPLE 8

The mouse mammary tumor cell line (MMT) described supra was used. Using the protocols set forth, supra, implants were prepared which contained 120,000 cells per bead, and 240,000 cells per bead.

The experimental model used was the mouse model, supra. Twenty-two mice were divided into groups of 4 (control), 9 and 9. The first group, i.e., the controls, were further divided into three groups: two received implants of one empty bead, one received two empty beads, and one received three empty beads.

Within experimental Group A (9 animals), the beads contained 120,000 cells, while in experimental Group B, the beads contained 240,000 cells. Within Groups A and B, there were three subdivisions, each of which contained three mice. The subgroups received one, two, or three beads containing MMT cells.

For the first few days, the mice in Groups A and B were lethargic, with spiky hair. This persisted for about five days, after which normal behavior was observed. Twenty-one days following implantation, all animals received injections of 40,000 RENCA cells.

After another twenty days, the control mice exhibited distended abdomens, and extremely spiky hair. One control mouse died twenty-five days following injection, while the remaining control mice appeared terminal. All mice were sacrificed, and tumor development was observed. These observations are recorded in Table 3 infra:

TABLE 3

| NUMBER OF MACROBEADS IN MICE | CONTROL | EXPERIMENTAL GROUP A | EXPERIMENTAL GROUP B |
| --- | --- | --- | --- |
| 1 | ++++ | − | − |
| 1 | ++++ | − | − |
| 1 |  | + | ++ |
| 2 | ++++ | − | − |
| 2 |  | − | − |
| 2 |  | ++ | ++ |
| 3 | ++++ | − | − |
| 3 |  | − | − |
| 3 |  | − | +++ |

These results show that, of eighteen mice treated, thirteen showed no disease. Of the mice in Group A, one mouse exhibited a few small nodules (+), and another mouse showed a few tumors (++).

Within Group B, one mouse which had received one bead, and one mouse which received two beads showed a few tumors, entangled with intestine. One of the mice which received three beads had developed a large solid tumor and was apparently very sick (+++). All control mice had numerous tumors (++++). The results showed that the encapsulated mouse mammary tumor cells inhibited tumor formation.

EXAMPLE 9

As suggested, supra, the practice of the invention results in the production of material which inhibits and/or prevents tumor cell proliferation. This was explored further in the experiment which follows.

Additional beads were made, as described supra in example 2, except that atelocollagen was not included. Hence, these beads are agarose/agarose beads. RENCA cells, as described, supra, were incorporated into these beads, again as described supra.

Two sets of three six-well plates were then used as control and experimental groups. In the control group, wells were filled with 4 ml of RPMI complete medium (10% fetal calf serum and 11 ml/l of penicillin). Each control group well was then inoculated with 10,000 RENCA cells.

In the experimental group, the RPMI complete medium was conditioned, by adding material secured by incubating ten RENCA containing beads (120,000 cells per bead), in a 35×100 mm petri plate containing 50 ml of the RPMI complete medium. Following five days of incubation, medium was collected from these plates, and 4 ml of it was placed in each test well. These wells were then inoculated with 10,000 RENCA cells in each.

All plates (both control and experimental) were incubated at 37° C. for five days. Following the incubation period, cells were trypsinized, washed, pooled, and counted using a hemocytometer. The results are shown in Table 4:

TABLE 4

| TEST WELL # | RENCA CELLS WITH CONTROL MEDIUM | RENCA CELLS WITH CONDITIONED MEDIUM |
| --- | --- | --- |
| 1 | $7 \times 10^5$ | $3 \times 10^5$ |
| 2 | $8 \times 10^5$ | $2.5 \times 10^5$ |
| 3 | $7 \times 10^5$ | $3.4 \times 10^5$ |

These results show that the cells, when restricted in, e.g., the beads of the examples, produced some material which resulted in suppression of tumor cell proliferation.

EXAMPLE 10

The experiment set forth supra showed that RENCA cell growth, in conditioned medium, was about half the growth of the cells in control medium. The experiments set forth herein examined whether the suppression of proliferation would continue after the conditioned medium was frozen.

RENCA conditioned medium was prepared by incubating ten RENCA containing beads for five days. Incubation was in 35×100 mm petri plates, with 50 ml RMPI complete medium, at 37° C. Following the incubation, the medium was collected and stored at −20° C. Conditioned medium was prepared by incubating MMT (mouse mammary tumor) cell containing beads. The beads contained 240,000 cell per bead; otherwise all conditions were the same.

Frozen media were thawed at 37° C., and then used in the following tests. Three six-well plates were used for each treatment, i.e., (i) RMPI control medium, (2) RENCA frozen conditioned medium, and (3) MMT frozen conditioned medium. A total of 4 ml of medium was dispensed into each well. All wells were then inoculated with 10,000 RENCA cells, and incubated at 37° C., for five days. Following incubation, two plates of samples were taken from each well, trypsinized, washed, pooled, and counted in a hemocytometer. At eight days, the remaining three plates of each well were tested in the same way.

Results follow:

TABLE 5

| DISH | CONTROL MEDIUM | FROZEN CONDITIONED MEDIUM OF RENCA | FROZEN CONDITIONED MEDIUM OF MMT |
|---|---|---|---|
| 5 DAYS OLD | | | |
| 1 | $6 \times 10^5$ | $5 \times 10^5$ | $8 \times 10^4$ |
| 2 | $6.8 \times 10^5$ | $4.2 \times 10^5$ | $8.5 \times 10^4$ |
| 8 DAYS OLD | | | |
| 3 | $2.8 \times 10^6$ | $2 \times 10^6$ | $8 \times 10^4$ |

When these results are compared to those in example 6, supra, it will be seen that, while the frozen/thawed RENCA conditioned medium did not suppress proliferation to the same extent that frozen/thawed MMT conditioned medium did (compare examples 6 and 7), it did, nonetheless, suppress proliferation.

EXAMPLE 11

The experiments set forth supra showed that frozen conditioned medium from RENCA- or MMT-containing macrobeads inhibits the proliferation of RENCA cells in vitro. The experiments set forth herein examined whether RENCA- or MMT-macrobead conditioned medium, prepared as 30 kd or 50 kd concentrates by filtration, would inhibit the proliferation of RENCA cells in vitro. The effects of macrobead conditioned media were compared to the effects of media conditioned in the presence of unrestricted RENCA and MMT cells growing in monolayer cultures, to determine whether unrestricted tumor cells grown to confluence also make proliferation regulating material.

For these experiments, 10 macrobeads, each containing 120,000 RENCA or MMT cells (i.e., $1.2 \times 10^6$ cells total) were used to condition the medium (complete RPMI) over a period of 5 days. In parallel, $1.2 \times 10^6$ RENCA or MMT cells, i.e., the same number of cells, were plated in a culture dish and allowed to proliferate as a monolayer over a period of 4 days in complete RPMI medium. Medium was then changed, and this medium was collected twenty-four hours later. The reason for the different length of time of exposure of the beads and unrestricted cells was the difference in cell numbers in the monolayers vs. the beads (3- to 5-fold more cells in the monolayers) at the end of the 5-day period. In other words, unrestricted cells grew so much more rapidly than encapsulated cells, that there were 3-5 times more cells.

30 kd and 50 kd filters were used to prepare concentrates of the conditioned media that would, presumably, contain the active material, and would also eliminate toxic metabolic and/or waste materials as confounding factors in the experiments. These contaminants, which are well known, are too small to be retained on a 30 kd filter. Filtrates were also tested, but any interpretation of the results with this material is complicated by the presence of the cellular waste products. A serum-free medium (AIM V) was also used in some experiments to be certain that any effects of serum per se were controlled.

Essentially, conditioned medium was collected, either three to five days after the macrobeads had been added to it, or twenty-four hours after new medium had been added to the unrestricted cells. The medium was then placed in a test tube filter with an appropriate filter (either a 30 kd or 50 kd filter), and centrifuged for 90 minutes. Material which remained on the filter is referred to as the "concentrate," while that which spins through the filter and collects at the bottom of the tube is the filtrate.

The results, summarized in the Table 6 which follow, show that when the conditioned medium resulting from the restricted RENCA cells in the macrobeads was used, this inhibited RENCA cell proliferation by about 52% in two separate experiments. The 50 kd concentrate inhibited proliferation by about 99%, in both cases, while the 30 kd concentrate inhibited proliferation by about 97%.

TABLE 6

Inhibition of RENCA Cell Growth in RENCA Macrobead Conditioned Medium and Reconstituted Concentrates

| Plate Number | Unconditioned RPMI Medium # of Cells | RENCA Macrobead Conditioned Medium | | 30K Concentrate of this Medium | | 50K Concentrate of this Medium | |
|---|---|---|---|---|---|---|---|
| | | # of Cells | Inhibition | # of Cells | Inhibition | # of Cells | Inhibition |
| 1 | $1.6 \times 10^6$ | $7.8 \times 10^5$ | 51.3% | $4.2 \times 10^4$ | 97% | $2.0 \times 10^4$ | 99% |
| 2 | $1.65 \times 10^6$ | $8.0 \times 10^5$ | 51.5% | $5.0 \times 10^4$ | 97% | $2.0 \times 10^4$ | 99% |

TABLE 7

Inhibition of RENCA Cell Growth in RENCA Cell Culture Conditioned Medium and Reconstituted Concentrates

| Plate Number | Unconditioned Medium # of Cells | RENCA Cell Culture Conditioned Medium # of Cells | Inhibition | 30K Concentrate of this Medium # of Cells | Inhibition | 50K Concentrate of this Medium # of Cells | Inhibition |
|---|---|---|---|---|---|---|---|
| 1 | $1.6 \times 10^6$ | $1.3 \times 10^6$ | 18.8% | $1.1 \times 10^6$ | 31.3% | $9.0 \times 10^5$ | 43.8% |
| 2 | $1.6 \times 10^6$ | $1.2 \times 10^6$ | 25.0% | $1.0 \times 10^6$ | 37.5% | $9.5 \times 10^5$ | 40.6% |

TABLE 8

Inhibition of RENCA Cell Growth in RENCA Macrobead Conditioned Medium and Concentrate (AIM V Medium)

| PLATE NUMBER | AIM V CONTROL MEDIUM | CONDITIONED MEDIUM # cells | % inhibition | 30K CONCENTRATE # cells | % inhibition | 50K CONCENTRATE # cells | % inhibition |
|---|---|---|---|---|---|---|---|
| 1 | $1.3 \times 10^6$ | $6.0 \times 10^5$ | 54% | $\sim 5.0 \times 10^4$ | 96% | $\sim 4.0 \times 10^4$ | 97% |
| 2 | $1.3 \times 10^6$ | $5.5 \times 10^5$ | 58% | $\sim 5.0 \times 10^4$ | 96% | $\sim 4.0 \times 10^4$ | 97% |

An important point of the experiment is that MMT cells and RENCA cells, when entrapped and restricted in the macrobeads both suppress RENCA cell proliferation, indicating that the proliferation-restrictive effect is not specific to tumor type. These experiments confirm those of Example 8 in which MMT-containing macrobeads suppressed the proliferation of RENCA cells in vivo. In addition, they extend the findings to indicate that the material released from the macrobeads into the medium contains molecules that are at least 30 kd in molecular weight which are responsible, in part, for the proliferation-restrictive effect. Finally, these experiments show that the macrobead-restricted RENCA and MMT cells produce far more of the proliferation-suppressing material than the same cells grown to confluency in monolayer cultures.

EXAMPLE 12

The experiments set forth above show that both MMT- and RENCA-macrobead conditioned media contain material released from the proliferation-restricted cells in the macrobead that can inhibit the proliferation of RENCA cells in vivo and in vitro. Importantly, the experiments show that the proliferation-inhibitory effect is not specific to tumor type. The experiments set forth herein examine whether the effect is also independent of the species in which the tumor originally arose. Here, the tumor cell proliferation-inhibitory effects of a human breast cancer-derived cell line on RENCA cells (using macrobeads and macrobead-conditioned media) and also MMT cells (using macrobead-conditioned media only) in vitro were examined.

The methodologies for these in vitro studies were similar to those described in the examples above. 100,000 MCF-7 cells, (human breast cancer cells) were encapsulated in macrobeads, and the resulting MCF-7 macrobeads were incubated with RENCA cells (10,000 per well) for 5 days to evaluate the proliferation-inhibitory effects of the macrobeads. In addition, MCF-7 macrobead-conditioned medium was prepared over a 5-day incubation period and tested on both RENCA and MMT cells. Cell proliferation was measured over a 5-day period.

The results are set forth below:

TABLE 9

RESULTS OF MCF-7 MACROBEADS ON RENCA TARGET CELLS

| Well # | CONTROL (Empty Macrobeads) | MCF-7 MACROBEADS |
|---|---|---|
| 1 | $8.4 \times 10^5$ | $4.4 \times 10^5$ |
| 2 | $8.0 \times 10^5$ | $4.4 \times 10^5$ |
| 3 | $7.4 \times 10^5$ | $3.8 \times 10^5$ |

TABLE 10

RESULTS OF MCF-7 CONDITIONED MEDIUM ON RENCA TARGET CELLS

| Plate | RPMI Control Medium | RPMI Conditioned Medium MCF-7 |
|---|---|---|
| 1 | $9.0 \times 10^5$ | $5.0 \times 10^5$ |
| 2 | $8.8 \times 10^5$ | $4.8 \times 10^5$ |

TABLE 11

RESULTS OF MCF-7 CONDITIONED MEDIUM ON MMT TARGET CELLS

| Plate | RPMI Control Medium | RPMI Conditioned Medium: MCF-7 |
|---|---|---|
| 1 | $5.0 \times 10^5$ | $1.5 \times 10^5$ |
| 2 | $6.0 \times 10^5$ | $1.8 \times 10^5$ |

The results show that MCF-7, a human breast adenocarcinoma cell line, when proliferation-restricted in macrobeads, produces a material that inhibits the proliferation of mouse renal adenocarcinoma cells and mouse breast cancer tumor cells to a significant degree (30-70%) as demonstrated by both the macrobeads themselves and conditioned media derived therefrom. This indicates that the proliferation-inhibitory effect of growth-restricted cancer cells is independent of both tumor type and species of tumor origin, i.e., mouse and human.

EXAMPLE 13

The experiments set forth above demonstrate that a human-derived breast adenocarcinoma cell line (MCF-7), when growth-restricted in macrobeads, produces proliferation inhibition of mouse renal and mouse breast adenocarcinoma cells in vitro. The experiments set forth herein examine whether a parallel effect of MCF-7-containing macrobeads on RENCA cell tumor growth in vivo exists.

Eighteen Balb/c mice were injected with 20,000 RENCA cells intraperitoneally. After three days the mice were divided into twogroups. Group 1 had six mice and Group 2 had the remaining twelve mice. Group 1 mice, the controls, were transplanted with three empty macrobeads each. Group 2 received three MCF-7-containing macrobeads (100,000 cells per bead). After twenty-five days, 2 mice from Group 1 and three mice from Group 2 were sacrificed. The same number were sacrificed on day twenty-six and the remaining mice were sacrificed on day twenty-seven.

On necroscopy, the peritoneal cavities of the control mice were observed to be completely packed with tumor, and the normal organs were difficult to identify. We classified this as ++++(100%) tumor intensity. In the treated mice, tumor intensity was rated at +(10-20%).

These results show that macrobeads containing human breast adenocarcinoma cells are capable of inhibiting renal cell adenocarcinoma tumor growth in mice, confirming again that the cancer-cell proliferation/tumor growth-inhibitory effect is neither type-specific nor species-specific.

EXAMPLE 14

The experiments set forth above demonstrate that the cell proliferation/tumor growth inhibitory effect of macrobead growth-restricted tumors is neither tumor-type nor species specific. The experiments set forth herein examine whether (macrobead) proliferation-restricted mouse breast adenocarcinoma cells can inhibit the growth of both spontaneous mammary tumors and tumors resulting from the injection of MMT cells.

C3H mice have a very high incidence of the development of mammary tumors over their life span. Seven mice at risk for the development of such tumors showed tumors at sixteen months of age. At this time, five of the seven mice were implanted with four MMT macrobeads containing 100,000 cells each. The remaining two control mice received four empty macrobeads each. The two control mice developed large tumors and died within three months after the bead implants. The treated mice were sacrificed eleven months after the MMT macrobead implants. The retrieved macrobeads, organs and tumors were examined grossly and histologically. Hernotoxylin & Eosin staining of the MMT macrobeads showed viable cells. The pre-existing tumors had not increased in size, and there was no evidence of any new tumor development.

Experiments in which MMT tumor cells were injected subcutaneously in the thoracic region were also performed. Fourteen C3H mice were divided into two groups. The five control group mice were implanted with three empty macrobeads each. The nine treated mice received three MMT-containing macrobeads (240,000 cells each). Three weeks after implantation all fourteen mice were injected subcutaneously in the mammary area with 20,000 MMT cells each.

Within twenty-five to thirty days, the five control group mice became ill with evident tumor formation, and all were dead by thirty-five days post-injection. The nine treated mice, observed weekly, continued without any evidence of tumor formation or ill health during this period. Ten to twelve months after tumor injection, four of the nine treated mice developed lumps and lost their fur in patches. The remaining five mice were implanted again with three MMT macrobeads thirteen months after the initial tumor injection. One mouse died three days after this surgery, but on necropsy was completely free of tumor. The four surviving mice were sacrificed eight months after the second macrobead implant. Necropsy showed minimal or no tumor proliferation.

An additional observation from these experiments was that the beads retrieved from the first implantation contained viable tumor cells based both on histology and their ability to resume aggressive tumor growth patterns in tissue culture after removal from the bead.

The results of these experiments show that the cell proliferation/tumor growth-inhibiting effects of macrobead-restricted cancer cells, in this case mouse mammary adenocarcinoma cells, can influence the development and growth of both spontaneously arising tumors and experimentally induced tumors arising from the injection of tumor cells into the mammary area.

EXAMPLE 15

The experiments set forth above demonstrate a tumor cell proliferation/tumor growth-inhibitory effect of macrobead proliferation-restricted cancer cells that is characterized by its effectiveness across tumor types and across species, as well as in both spontaneous and artificially-induced tumors. The experiments described herein extend these findings to examine the effects of macrobead-entrapped, proliferation-restricted human prostate adenocarcinoma-derived cells (ARCap10), mouse (Balb/c) renal adenocarcinoma cells (RENCA cells), and mouse (C3H) mammary adenocarcinoma cells (MMT) on the proliferation of ARCaP10 tumor cells and ARCaP10 tumor growth in nude (Nu/Nu) mice.

In the first series of experiments, fifteen Nu/Nu mice were injected with $2.5 \times 10^6$ ARCaP10 cells subcutaneously in the flank. On the twentieth day after injection, at which time the average maximal tumor diameter was 0.5 cm, the mice were divided into two groups. Nine were implanted with four ARCaP10 macrobeads ($1.0 \times 10^5$ cells per macrobead) each, and six control mice received four empty macrobeads each.

Ten weeks after implantation, five of the control mice had very large vascularized tumors (average 2.5 cm in diameter) and one mouse showed a slightly smaller tumor (less than 0.5 cm). In the treated group, five mice showed complete regression of the initial tumors, and all remained tumor free until sacrifice at eight months. Two mice showed no tumor growth, i.e., their tumors had the same maximal diameter as they had had at the time of implantation of the macrobeads, and two mice showed tumors that had enlarged since implantation of the macrobeads.

The results (tumor volume and size (l×w×h)) of an experiment in which RENCA-containing macrobeads ($1.2 \times 10^5$) were implanted eighteen days after subcutaneous flank injection of $3.0 \times 10^6$ ARCaP10 tumor cells per animal in 4 Nu/Nu mice are set forth below:

TABLE 12

SIZE OF TUMORS OBSERVED IN TREATED MICE (in mm)

| Treated Mouse Number | 3 Days Before Transplant (Mar. 3, 1998) | Day of Transplant (Mar. 6, 1998) | 3 Days After Transplant (Mar. 9, 1998) | 6 Days After Transplant (Mar. 12, 1998) | 10 Days After Transplant (Mar. 16, 1998) | 14 Days After Transplant (Mar. 20, 1998) |
|---|---|---|---|---|---|---|
| 1 | 3.5 × 3 × flat | 6.2 × 5.4 × flat | 4 × 4 × flat | disappearing | 0 | 0 |
| 2 | 3 × 3 × 1.5 | 5.1 × 2.2 × 2 | 4 × 2 × 0.5 | 3 × 3 × 0.4 | 2 × 2 × 0.3 | 2 × 2 × 0.3 |
| 3 | 3 × 2.5 × 1 | 3.1 × 3.3 × 1 | 3 × 2 × 0.5 | 3 × 2 × 0.2 | 3 × 2 × 0.2 | 3 × 2 × 0.2 |
| 4 | 2.5 × 2.5 × flat | 3.2 × 3.4 × 0.5 | speck under skin | 0 | 0 | 0 |

TABLE 13

VOLUME OF TUMORS OBSERVED IN TREATED MICE

| Treated Mouse Number | 3 Days Before Transplant (Mar. 3, 1998) | Day of Transplant (Mar. 6, 1998) | 3 Days After Transplant (Mar. 9, 1998) | 6 Days After Transplant (Mar. 12, 1998) | 10 Days After Transplant (Mar. 16, 1998) | 14 Days After Transplant (Mar. 20, 1998) |
|---|---|---|---|---|---|---|
| 1 | 2.76 | 8.81 | 1.68 | 0 | 0 | 0 |
| 2 | 7.10 | 11.81 | 2.10 | 1.89 | 0.63 | 0.63 |
| 3 | 3.95 | 5.38 | 1.58 | 0.63 | 0.63 | 0.63 |
| 4 | 1.64 | 2.86 | 0 | 0 | 0 | 0 |

In another experiment 10 Nu/Nu mice were injected with $2.5 \times 10^6$ APCaP10 cells, with six of the mice showing tumor development sixty-four days after injection. Three of these mice were given four MMT macrobeads ($2.4 \times 10^5$ cells each) and three received empty macrobeads. The results are set forth below:

TABLE 14

SIZE OF TUMORS OBSERVED IN TREATED MICE (in mm)

| Treated Mouse Number | 5 Days Before Transplant (Feb. 5, 1998) | Day of Transplant (Feb. 10, 1998) | 18 Days After Transplant (Feb. 28, 1998) | 22 Days After Transplant (Mar. 4, 1998) | 27 Days After Transplant (Mar. 9, 1998) | 30 Days After Transplant (Mar. 12, 1998) |
|---|---|---|---|---|---|---|
| 1 | 2 × 2 × 1 | 3 × 3 × 1.5 | 1 × 1 × 0.5 | 0 | 0 | 0 |
| 2 | 3 × 2 × 1 | 3 × 2.5 × 1 | 2 × 2 × flat | <1 mm | <0.8 mm | <0.8 mm |
| 3 | 4 × 4 × 1.5 | 6 × 6 × 1.5 | 6 × 2 × flat | 4 × 1 × flat | 3 × 1 × flat | 3 × 1 × flat |

TABLE 15

SIZE OF TUMORS OBSERVED IN CONTROL MICE (in mm)

| Control Mouse Number | 5 Days Before Transplant (Feb. 5, 1998) | Day of Transplant (Feb. 10, 1998) | 18 Days After Transplant (Feb. 28, 1998) | 22 Days After Transplant (Mar. 4, 1998) | 27 Days After Transplant (Mar. 9, 1998) | 30 Days After Transplant (Mar. 12, 1998) |
|---|---|---|---|---|---|---|
| 1 | 4 × 4 × 1.5 | 5 × 5 × 2 | 6.5 × 6 × 3 | 6.5 × 6 × 3 | 6.5 × 6 × 3 | 7 × 7 × 3 |
| 2 | 3 × 2 × 1 | 4 × 6 × 3 | 4.5 × 7 × 3 | 5 × 8 × 3 | 11 × 12 × 5 | 13.3 × 13.3 × 6.5; 2nd tumor: 6 × 6 × 1 |
| 3 | 5 × 4 × 1 | 5 × 4 × 2 | 5 × 4.6 × 2.5 (multilobe) | 5 × 5 × 2.5 | 6 × 6 × 2.5; 2nd tumor: 2 × 2 × 1 | 7 × 7 × 2.5; 2nd tumor: 3 × 3 × 0.5 |

The results of these experiments further confirm the cross-species, cross-tumor nature of the tumor growth-inhibiting effect of proliferation restriction on tumors of various types. In addition, these experiments demonstrate the ability of the proliferation-restricted cancer cells not only to suppress tumor growth and to prevent tumor formation, but also to cause actual regression of in vivo tumors.

EXAMPLE 16

The experiments set forth above showed that proliferation-restricted cancer cells from several types of tumors and species can inhibit the proliferation of the same and different cancer cell types in vitro and prevent the formation of both spontaneous and induced tumors, prevent the growth of tumors, and cause tumors to regress in vivo in an effect that is independent of species and cancer type. The experiment set forth herein describes the extension of the findings to another species (rabbit) and a rabbit tumor known to have been induced virally (VX2).

In this experiment, a New Zealand White Rabbit (2.5 lbs.) was injected intramuscularly in one thigh (two sites) with 0.5 ml of a VX2 tumor slurry (characterized as being able to pass through a #26 gauge needle) at each site. At 3.5 weeks, a 5 cm×2.5 cm (l×w) tumor had appeared on the dorsal thigh and two 3 cm-diameter tumors were present on the ventral thigh. At this point, 211 macrobeads (108 RENCA cell beads, 63 MMT cell beads, and 40 MCF-7 human breast cancer cell-containing beads) were implanted intraperitoneally. Within two days, the tumor on the dorsal thigh had shrunk by approximately 50%; however, the two ventral tumors did not change. The animal was sacrificed ten days after macrobead implantation. On necropsy, there was a clear difference between the dorsal and ventral tumors in that the former was much smaller than it had been at the time of macrobead implantation, whereas the two ventral tumors were both hemorrhagic and necrotic.

This experiment extends the findings of the effectiveness of proliferation restriction of various types of cancer cells in relation to the prevention, arrest, and even regression of tumor growth to another species, the rabbit, adds a tumor of known viral origin to the list of cancer types, and further supports the cross-tumor and cross-species nature of the growth inhibiting effect, since a combination of mouse renal, mouse breast and human breast cancer cell-containing macrobeads were used. In addition, the experiment adds a larger animal model to the in vivo testing of the effectiveness of proliferation-restriction of cancer cells for the treatment of cancer.

EXAMPLE 17

The experiments set forth above show that proliferation-restriction of various types of tumor cells results in their ability to inhibit the growth of cells of the same or different type in vitro and to prevent the formation of, suppress the growth of, or cause regression of various types of tumors in vivo and that the effects seen are independent of tumor type and species. The experiments set forth herein evaluated the long-term viability of the proliferation-restricted RENCA cancer cells in agarose-agarose macrobeads maintained in culture over periods of 1 month, 6 months, 2 years, and 3 years using histological, culture, and in vivo techniques. MMT-containing macrobeads were maintained in culture for up to six months. In addition, RENCA- and MMT-containing macrobeads retrieved from Balb/c and C3H mice respectively after periods of 2 to 8 months after implantation were examined for viable tumor cells by both histological and culture techniques.

For these experiments the agarose-agarose macrobeads were prepared with either $1.2 \times 10^5$ RENCA cells or $2.4 \times 10^5$ MMT cells. They were examined histologically (hermatoxylin & eosin staining) and by culture techniques for cell viability and tumor characteristics at the intervals described supra. For the RENCA macrobeads, cell numbers increased approximately 3- to 5-fold over the first month with a subsequent additional doubling in six months. After one year, there was a continued increase in cellular mass, but the rate of cell proliferation had decreased. After two years, amorphous material had begun to appear in the center of the bead, and the cell mass/numbers did not appear to be increasing, although mitotic figures are still evident. After three years, there appeared to be somewhat more amorphous material in the center of the bead, but the cell mass/number was stable. MMT macrobeads have been followed for only six months, but the early pattern of cell proliferation and bead appearance is similar to that of RENCA.

For evaluation of the viability and biological behavior of the RENCA and MMT cells at the intervals described above, ten beads were crushed and plated in two or more 25 cm² tissue culture flasks in complete RPMI medium. The flasks were then observed for cell growth. At one and six month intervals, the number of viable cells retrievable from the beads increases. At one year, the number of RENCA cells growing from the crushed bead appears to be similar to that at six months. At two and three years, the proportion of viable cells appears to be somewhat less, dropping to approximately 20% of the maximum number they reached in the bead (i.e., in their restricted state) after three years in culture.

For the evaluation of the retrieved RENCA and MMT macrobeads after in vivo implantation (periods of 1-4 years for RENCA macrobeads and up to 8 months for MMT macrobeads), histological techniques have been utilized to date. The patterns of cell proliferation and mass are very similar to those of the beads maintained in culture for the corresponding periods of time, i.e., the cells increase in number at least up to 4 months for RENCA and 8 months for MMT.

For the other cancer cell lines with which we have been working, such as MCF-7 and ARCaP10, the viability patterns in macrobeads are similar to those observed for RENCA and MMT.

These experiments show that cancer cells can be maintained in vitro for periods of up to 3 years and in vivo for periods of at least 8 months in a proliferation-restricting environment and that they maintain their viability for these periods with clear demonstration of increasing cell numbers up to at least one year. This is important not only for the ability to create and store cancer treatment materials, but also for the ability of the proliferation-restricted cells to put out tumor growth suppressing material in warm-blooded animals over the continuous, prolonged periods likely to be necessary for the successful treatment of experimental or naturally-occurring cancer.

EXAMPLE 18

The experiments set forth above show that cancer cells of various types can be maintained under proliferation-restricted conditions for long periods of time (up to 3 years) with retention of their ability to proliferate, form tumors, and release cell-proliferation-inhibiting and tumor-growth preventing, suppressing, and even regressive materials. The experiments set forth herein evaluate the possible toxicity of long-term (one-year) implants of cancer cell-containing, agarose-agarose macrobeads in Balb/c mice.

Seven Balb/c mice were implanted with 3 RENCA macrobeads each ($1.2 \times 10^5$ cells per bead). Immediately after surgery the mice appeared ill (spiky fur and lethargy) for a few days, but became healthy again after this. All mice survived in apparent good health for a period of at least one year, with one mouse dying of old age and another of unrelated causes. All mice were sacrificed. On necropsy, no abnormalities, such as fibrosis, peritonitis, or tumor growth were observed. All organs observed appeared normal, although some adherence of the beads to the serosal surfaces of the intestines were observed, especially where there were intestinal loops. No interference with the normal function or structure of the intestines has been observed.

These results show that cancer cell-containing agarose-agarose macrobeads are well tolerated in experimental animals over a one-year period. These findings show that the proliferation-restricting cancer-cell beads can be utilized in vivo for the prevention, suppression and regression of the growth of in vivo tumors of various types.

The foregoing examples describe the invention, which includes, inter alia, compositions of matter which can be used to produce material which suppresses proliferation of cancer. These compositions comprise cancer cells entrapped in a selectively-permeable material to form a structure which restricts the proliferation of the entrapped cells. As a result of their being restricted, the cells produce unexpectedly high amounts of material which suppresses proliferation of cancer cells. The restricted cells produce more of the material than comparable, non-restricted cancer cells.

The matter used to make the structures of the invention include any biocompatible matter which restricts the growth of cancer cells, thereby inducing them to produce greater amounts of cancer cell proliferation/tumor growth-suppressing material. The structure has a suitable pore size such that the above material can diffuse to the external environment, and prevent products or cells from the immune system of the host from entering the structure and causing the rejection of or otherwise impair their ability to survive and continue to produce the desired material. The matter used to form the structure will also be capable of maintaining viable (proliferation-restricted, but surviving) cells both in vitro and in vivo, preferably for periods of up to several years by providing for the entrance of proper nutrients, the elimination of cellular waste products, and a compatible physico-chemical intra-structural environment. The matter used to prepare the structure is preferably well tolerated when implanted in vivo, most preferably for the entire duration of implantation in the host.

A non-limiting list of materials and combinations of materials that might be utilized includes alginate-poly-(L-lysine); alginate-poly-(L-lysine)-alginate; alginate-poly-(L-lysine)-polyethyleneimine; chitosan-alginate; polyhydroxylethyl-methacrylate-methyl methacrylate; carbonylmethylcellulose; K-carrageenan; chitosan; agarose-polyethersulphone-hexadi-methirine-bromide (Polybrene); ethyl-cellulose; silica gels; and combinations thereof.

The structures which comprise the compositions of matter may take many shapes, such as a bead, a sphere, a cylinder, a capsule, a sheet or any other shape which is suitable for implantation in a subject, and/or culture in an in vitro milieu. The size of the structure can vary, depending upon its eventual use, as will be clear to the skilled artisan.

The structures of the invention are selectively permeable, such that nutrients may enter the structure, and so that the proliferation-inhibiting material as well as cellular waste may leave the structure. For in vivo use, it is preferred that the structures prevent the entry of products or cells of the immune system of a host which would cause the rejection of the cancer cells, or otherwise impair their ability of the cancer cells producing the proliferation-suppressive material.

Another aspect of the invention includes compositions which are useful in suppressing cancer cell proliferation. These compositions are prepared by culturing restricted cells as described supra in an appropriate culture medium, followed by recovery of the resultant conditioned medium. Concentrates can then be formed from the conditioned medium, e.g., by separating fractions having molecular weight of greater than 30 kd or greater than 50 kd, which have high anti-proliferative effect on cancer cells.

As the examples show, the invention is not limited to any particular type of cancer; any neoplastic cell may be used in accordance with the invention. Exemplary types of cancer cells which can be used are renal cancer cells, mammary cancer cells, prostate cancer cells, choriocarcinoma cells and so forth. The cancer cells may be of epithelial, mesothelial, endothelial or germ cell origin, and include cancer cells that generally do not form solid tumors such as leukemia cells.

As will be clear from this disclosure, a further aspect of the invention is therapeutic methods for treating individuals suffering from cancer. When used in a therapeutic context, as will be elaborated upon infra, the type of cancer cell restricted in the structure need not be the same type of cancer from which the subject is suffering, although it can be. One such method involves inserting at least one of the structures of the invention into the subject, in an amount sufficient to cause suppression of cancer-cell proliferation in the subject. Preferably, the subject is a human being, although it is applicable to other animals, such as domestic animals, farm animals, or any type of animal which suffers from cancer.

The composition of the present invention can be used as primary therapy in the treatment of cancer, and as an adjunct treatment in combination with other cancer therapies. For example, patients may be treated with compositions and methods described herein, in conjunction with radiation therapy, chemotherapy, treatment with other biologically active materials such as cytokines, anti-sense molecules, steroid hormones, gene therapy, and the like. Additionally, the compositions and methods of the invention can be used in conjunction with surgical procedures to treat cancer, e.g., by implanting the macrobeads after resection of a tumor to prevent regrowth and metastases. Cancers which present in an inoperable state may be rendered operable by treatment with the anti-proliferative compositions of the invention.

The compositions of the invention can also be used prophylactically in individuals at risk for developing cancer, e.g., presence of individual risk factors, family history of cancer generally, family history of cancer of a specific type (e.g. breast cancer), and exposure to occupational or other carcinogens or cancer promoting agents. For prophylaxis against cancer, a prophylactically effective amount of the structures of the invention are administered to the individual upon identification of one or more risk factors.

As indicated by the examples, supra, the antiproliferative effect is not limited by the type of cancer cell used, nor by the species from which the cancer cell originated. Hence, one can administer structures which contain cancer cells of a first type to a subject with a second, different type of cancer. Further, cancer cells of a species different from the species being treated can be used in the administered structures. For example, mouse cancer cells may be restricted in the structures of the invention, and then be administered to a human. Of course, the structures may contain cancer cells from the same species as is being treated. Still further, the cancer cells may be taken from the individual to be treated, entrapped and restricted, and then administered to the same individual.

Yet another aspect of the invention is the use of concentrates, as described herein, as a therapeutic agent. These concentrates may be prepared as described herein, and then be administered to a subject with cancer. All of the embodiments described supra may be used in preparing the concentrates. For example, following in vitro culture of structures containing mouse cancer cells, concentrates can be prepared and then administered to humans. Similarly, the structures can contain human cells, and even cells from the same individual. Also, as discussed supra, the type of cancer cell used to prepare the concentrate may be, but need not be, the same type of cancer as the subject suffers from. Hence, murine mammary cancer cells may be used, e.g., to prepare a concentrate to be used to treat a human with melanoma, or an individual with prostate cancer may have some of his prostate cancer cells removed, entrapped in a structure of the invention, cultured in an appropriate medium, and then have resulting conditioned medium filtered to produce a concentrate. It should be borne in mind that the conditioned media resulting from in vitro cultures of the structures of the invention is also a part of the invention.

Processes for making the structures of the invention, as well as the concentrates of the invention, are also a part of the invention. In the case of the concentrates, one simply cultures the structures of the invention for a time sufficient to produce a sufficient amount of antiproliferative material and then separates the desired portions from the resultant conditioned medium, e.g., by filtration with a filter having an appropriate cut off point, such as 30 kilodaltons or 50 kilodaltons.

Other facets of the invention will be clear to the skilled artisan, and need not be set out here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A composition of matter comprising a solid, agarose coated, agarose and collagen bead, wherein said bead contains cancer cells isolated from an animal which, when restricted by being entrapped in said bead, produce more of a material that suppresses cancer cell proliferation, wherein said material diffuses through said solid, agarose coated, agarose and collagen bead.

2. The composition of matter of claim 1, wherein said cancer cells are renal cancer cells.

3. The composition of matter of claim 1, wherein said bead contains from about 10,000 to about 200,000 cells.

4. The composition of matter of claim 3, wherein said bead contains from about 30,000 to about 100,000 cells.

5. Method for suppressing cancer cell proliferation in a subject, comprising implanting a sufficient amount of the composition of matter of claim 1 in said subject to suppress the proliferation of cancer cells in subject.

6. A process for making a solid bead which comprises agarose and collagen, and is coated with agarose, wherein said solid bead contains cancer cells which, when restricted by being entrapped in said bead produce material that suppresses cancer cell proliferation and diffuses through said bead, comprising:

(a) adding agarose and collagen to a solution which contains a sample of cancer cells isolated from an animal which are capable of producing material that suppresses cancer cell proliferation which diffuses through said bead when said cancer cells are restricted by being entrapped by the bead, (b) forming a semi-solid bead comprising said agarose and collagen and said cancer cells, (c) polymerizing the collagen in said semi-solid bead to form a solid, agarose and collagen bead containing and thereby restricting said cancer cells, and (d) coating said solid, agarose and collagen containing bead containing the restricted cancer cells with agarose, wherein said restricted cancer cells produce more of said material than when said cancer cells are not entrapped in said coated bead.

7. The process of claim 6, wherein said solution contains from about 10,000 to about 200,000 cells.

8. The process of claim 7, wherein said solution contains from about 30,000 cells to about 100,000 cells.

* * * * *